US011452746B2

(12) United States Patent
De Vos et al.

(10) Patent No.: US 11,452,746 B2
(45) Date of Patent: *Sep. 27, 2022

(54) BACTERIA-COMPRISING COMPOSITIONS AND METHODS OF USING THE SAME FOR TREATING AND/OR PREVENTING GASTROINTESTINAL, METABOLIC AND/OR OTHER DISEASES

(71) Applicant: Wageningen Universiteit, Wageningen (NL)

(72) Inventors: Willem Meindert De Vos, Ede (NL); Thi Phuong Nam Bui, Bennekom (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 410 days.

This patent is subject to a terminal disclaimer.

(21) Appl. No.: 15/542,311

(22) PCT Filed: Jan. 8, 2016

(86) PCT No.: PCT/EP2016/050310
§ 371 (c)(1),
(2) Date: Jul. 7, 2017

(87) PCT Pub. No.: WO2016/110585
PCT Pub. Date: Jul. 14, 2016

(65) Prior Publication Data
US 2018/0353552 A1 Dec. 13, 2018

(30) Foreign Application Priority Data
Jan. 9, 2015 (EP) ..................................... 15150701

(51) Int. Cl.
| | |
|---|---|
| *A61K 35/741* | (2015.01) |
| *A61K 45/06* | (2006.01) |
| *C12N 1/20* | (2006.01) |
| *A61P 1/04* | (2006.01) |
| *A61P 35/00* | (2006.01) |
| *C12R 1/01* | (2006.01) |

(52) U.S. Cl.
CPC ............ *A61K 35/741* (2013.01); *A61K 45/06* (2013.01); *A61P 1/04* (2018.01); *A61P 35/00* (2018.01); *C12N 1/205* (2021.05); *C12R 2001/01* (2021.05)

(58) Field of Classification Search
CPC ......... A61K 35/741; A61K 45/06; A61P 1/04; A61P 35/00; C12N 1/205; C12R 2001/01
USPC ....................................................... 424/93.4
See application file for complete search history.

(56) References Cited

U.S. PATENT DOCUMENTS

2014/0242654 A1  8/2014  Levinson

FOREIGN PATENT DOCUMENTS

| EP | 1835021 A1 | 9/2007 |
|---|---|---|
| WO | 2013032328 A1 | 3/2013 |
| WO | 2014150094 A1 | 9/2014 |
| WO | 2016110585 A1 | 7/2016 |

OTHER PUBLICATIONS

Vrieze et al., Transfer of Intestinal Microbiota from Lean Donors Increases Insulin Sensitivity in Individuals with Metabolic Syndrome, Gastroenterology, vol. 143, No. 4, 2012, p. 913-916.*
Turnbaugh et al., A core gut microbiome in obese and lean twins, Nature, Jan. 2009, 457(7228): p. 480-484.*
Yokoyama et al. "Complete Genomic Sequence of the O-Desmethylangolensin-Producing Bacterium Clostridium rRNA Cluster XlVa Strain SY8519, Isolated from Adult Human Intestine" Journal of Bacteriology, Oct. 2011, p. 5568-5569 vol. 193, No. 19; Copyright © 2011, American Society for Microbiology.
Barker et al., Pathway of lysine 1-3 degradation in Fusobacterium nucleatum Journal of bacteriology, Oct. 1, 1982, pp. 201-207.
Carrol et al.. The 1-16 gastrointestinal microbiome: a malleable, third genome of mammals, Mammalian Genome, vol. 20, Jul. 21, 2009 pp. 395-403.
PCT International Search Report, PCT/EP2016/050310, dated Feb. 2, 2016.
PCT International Search Report and Written Opinion, PCT/EP2016/050310, dated Feb. 2, 2016.
Klaring et al., *Intestinimonas butyriciproducens* gen. nov., sp. nov., a butyrate-producing bacterium from the mouse intestine, International Journal of Systematic and Evolutionary Microbiology, Aug. 5, 2013, vol. 63, pp. 4606-4612.
Pfleiderer et al.,Culturomics identified 11 new bacterial species from a single anorexia nervosa stool sample, European Journal of Clinical Microbiology & Infectious Diseases, vol. 32, Nov. 1, 2013, pp. 1471-1481.
Potrykus et al., Proteomic 1-3 investigation of amino acid catabolism in the indigenous gut anaerobe *Fusobacterium varium* Proteomics! vol. 8, No. 1, Jul. 1, 2008 pp. 2691-2703.
Solanki et al., Development 13 of Microencapsulation Delivery System for Long-Term Preservation of Probiotics as Biotherapeutics Agent, Biomed Research International, vol. 1, No. 8212, Jan. 1, 2013, pp. 151-121.
Tuohy et al., Metabolism of Maillard reaction products by the human gut microbiota—Implications for health, Mol. Nutr. Food Res., 2006, 50, 847-857.
Vital et al.. Revealing the bacterial butyrate synthesis pathways by analyzing (Meta)genomic data, Apr. 22, 2014, Center for Microbial Ecology, vol. 5, Issue 2.

(Continued)

*Primary Examiner* — Jennifer M.H. Tichy
(74) *Attorney, Agent, or Firm* — TraskBritt

(57) ABSTRACT

The disclosure is concerned with a novel human intestinal isolate capable of converting L-lysine into butyrate and/or of converting fructose-lysine into butyrate. The novel isolate can be used as a probiotic or supplement to promote production of butyrate in the GI tract, thereby preventing and/or treating conditions or diseases that benefit from the production of butyrate. Additionally, the isolate may prevent and/or treat conditions or diseases caused by an excess of pathogenic bacteria in the GI tract, mediated by L-lysine, or mediated by fructose-lysine or other advanced glycation end products.

19 Claims, 1 Drawing Sheet

(56) References Cited

OTHER PUBLICATIONS

European Communication pursuant to Article 94(3) EPC for European Application No. 16700202, dated Oct. 11, 2018, 3 pages.
Bui et al. "Production of butyrate from lysine and the Amadori product fructoselysine by a human gut commensal" Nature Communications vol. 6, Article No. 10062, 2015.

* cited by examiner

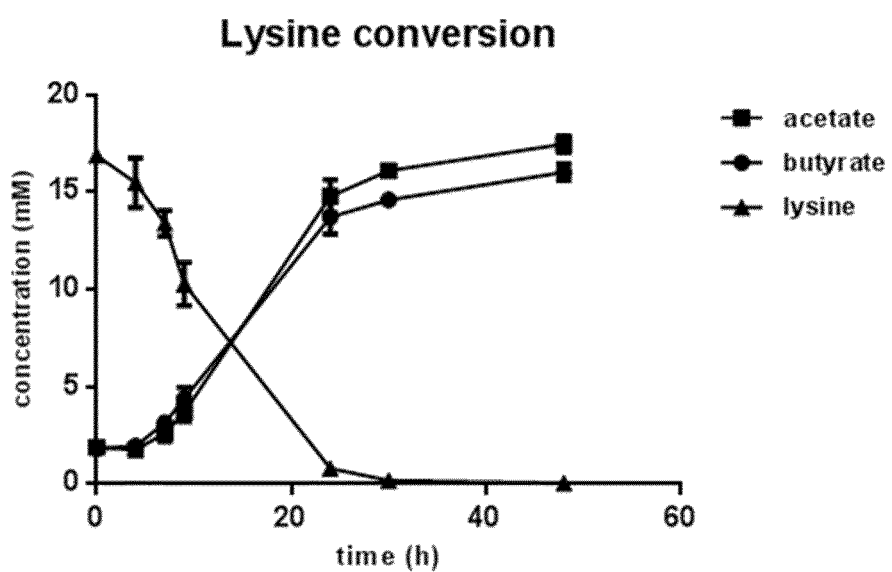

BACTERIA-COMPRISING COMPOSITIONS AND METHODS OF USING THE SAME FOR TREATING AND/OR PREVENTING GASTROINTESTINAL, METABOLIC AND/OR OTHER DISEASES

CROSS-REFERENCE TO RELATED APPLICATIONS

This application is a national phase entry under 35 U.S.C. § 371 of International Patent Application PCT/EP2016/050310, filed Jan. 8, 2016, designating the United States of America and published in English as International Patent Publication WO 2016/110585 A1 on Jul. 14, 2016, which claims the benefit under Article 8 of the Patent Cooperation Treaty to European Patent Application Serial No. 15150701.9, filed Jan. 9, 2015.

TECHNICAL FIELD

This disclosure relates to the fields of intestinal microbiota, metabolic conversions and pharmaceutical, food, or feed compositions comprising bacteria. More specifically, the disclosure provides a new intestinal bacterial strain isolated from a human, i.e., a human intestinal isolate, which is capable of converting L-lysine into butyrate, and which is further capable of converting glycated lysine into butyrate. Compositions comprising the intestinal bacterial strain and methods employing the intestinal bacterial strain are also provided.

BACKGROUND

The human gastrointestinal (GI) tract is inhabited by more than 100 trillion microorganisms (i.e., bacteria, archaea, fungi and viruses), which altogether form the so-called "gastrointestinal microbiota" (GI microbiota). The GI microbiota benefit from the host (e.g., human being) by being provided with substrates for fermentation that are either ingested by the host via the diet or are produced by the host itself, such as mucus, antibodies or digestive enzymes. In the host, the GI microbiota serve a wide array of functions including fermenting substrates into short chain fatty acids (SCFAs) that are used by the host, detoxifying undesired compounds, training the immune system, stimulating intestinal cell growth (e.g., intestinal epithelial cells), preventing growth of harmful pathogenic bacteria, regulating the development of the gut, producing vitamins for the host, such as biotin and vitamin K, producing hormones to direct the host to store fats, reducing the colonic pH, stimulating water and sodium absorption, and promoting gastrointestinal and metabolic health in general. There are intimate interactions between the GI tract at the one hand and other organs in the body, such as liver, adipose tissue and brain, explaining the large impact of GI microbiota on the health of the host. Moreover, as the GI microbiota is modulated strongly by diet, the role of the GI microbiota in dietary conversions is of high importance. The GI microbiota composition varies across individuals and apart from the diet is influenced by various other factors such as genes, age, and use of antibiotics (Salonen and de Vos, *Annu. Rev. Food Sci. Technol.* 2014, 5:239-62).

Variations in the GI microbiota may cause pathogenic species to multiply and subsequently outnumber the beneficial bacterial species. Beneficial bacterial species are associated with an array of beneficial effects, including the production of important nutrients and vitamins, the promotion of growth and integrity of intestinal cells, as well as the promotion of immunity through protection against pathogenic species. A well-studied beneficial function of intestinal bacteria is the production of one of the SCFAs, butyrate or butyric acid, by so-called butyrogenic bacteria. At the intestinal level, butyrate plays a regulatory role on the transepithelial fluid transport, ameliorates mucosal inflammation and oxidative status, reinforces the epithelial defense barrier, and modulates visceral sensitivity and intestinal motility. In addition, a growing number of studies have stressed the role of butyrate in the prevention and inhibition of colorectal cancer. At the systemic level, butyrate exerts potentially useful effects on many conditions, including hemoglobinopathies and other genetic or metabolic diseases, such as hypercholesterolemia, insulin resistance, and ischemic stroke (Canani et al., *World J. Gastroenterol.* 2011, 17:1519-28). Only a limited number of anaerobic intestinal bacteria are known to produce butyrate. Notably, butyrogenic bacteria are depleted in the GI tract of patients with metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes) (Hartstra et al., *Diabetes Care* 2015, 38:159-165).

An excess of pathogenic bacterial species in the GI tract, which is often associated with a reduction of butyrogenic bacteria in the GI tract, has been involved in several immune-related, inflammation-related and other disease conditions, including cancer (e.g., colorectal cancer), inflammatory bowel disease (IBD) (e.g., Crohn's disease, ulcerative colitis), irritable bowel syndrome (IBS), type 2 diabetes mellitus, obesity, bacterial or viral diarrhea, constipation, bloating, allergies, urinary tract infections, and others.

Moreover, diet is an important driver of disease and specific components of the diet may contribute to diseases indirectly via GI bacteria. This specifically relates to so called Advanced Glycation End products (AGEs). AGEs are formed via glycation reactions that occur through the formation of a Schiff base intermediate followed by an Amadori rearrangement to give the ketoamine adduct. When glucose is the reducing sugar, the Amadori rearrangement product is known as fructose-lysine. Spontaneous chemical conversion under slight alkaline conditions can result in further rearrangement, fragmentation and oxidation reactions of fructose-lysine, resulting in the formation of well-known AGEs, such as $N^\varepsilon$-(carboxymethyl)lysine (Hellwig and Henle, *Angew. Chem. Int. Ed.* 2014, 53:10316-10329). Thus, fructose-lysine is a pivotal product in AGE formation, the more so as glucose is among the most abundant sugars and lysine is among the most abundant amino acids on this planet. Fructose-lysine is used as an indicator for AGE formation and the fructose-lysine content can be very high in heated foods such as milk powder, evaporated milk or some pasta products. AGEs have been implicated in a variety of diseases, such as metabolic syndrome, type 2 diabetes mellitus, cardiovascular disease, ovarian aging, polycystic ovary syndrome and neurodegenerative disorders, such as Alzheimer's disease, multiple sclerosis and dementia. Certain GI bacteria—but not butyrogenic bacteria—have been implied in the metabolic conversions of AGEs (Tuohy et al., *Mol. Nutr. Food Res.* 2006, 50:847-857 DOI 10.1002/mnfr.200500126 847).

In the GI tract, L-lysine can be converted into toxic compounds that promote hepatic encephalopathy or cardiovascular diseases (Fujita et al., *Clin. Chim. Acta.* 1999, 287(1-2):99-109; Tang et al., *J. Card. Fail.* 2013, 19(4):219-224).

Several products and methods have been developed to help restore the balance between beneficial and pathogenic bacterial species or to increase the number of beneficial bacterial species and/or decrease the number of pathogenic bacterial species so as to prevent and/or treat conditions resulting from deleterious bacterial variations (e.g., excess pathogenic bacterial species and/or insufficiency of beneficial bacterial species) in the GI microbiota. Among some of the most commonly used products dedicated to improve and/or restore GI health are the so-called "prebiotic" and "probiotic" products. Fecal microbiota transplants have also been used, albeit less frequently, and an emerging field is the use of synthetic communities of specific bacteria isolated from the GI tract.

Probiotic products essentially consists of live microorganisms, which—when administered in effective amounts—confer a health benefit on the host (e.g., human being). Probiotics are typically used to increase the population of beneficial bacterial species in the gut or to help repopulate the gut with beneficial intestinal bacteria and compensate for deficiencies, for example, such as resulting from the use of antibiotics, disease, aging and/or poor nutrition. While probiotics are living microorganisms that help maintain a healthy GI, prebiotics are the substances that help fuel the beneficial intestinal bacteria. More specifically, prebiotics consist mainly of fermentable fibers or non-digestible carbohydrates that stimulate the growth and activity of these beneficial intestinal bacteria. The fermentation of these fibers by the beneficial bacteria promotes the production of beneficial end products, such as SCFAs.

Several probiotic products exist on the market in the form of compositions, beverages (e.g., dairy beverages, fermented beverages, etc.), formulations, food (e.g., yogurt, cheese, etc.) or nutritional supplements (e.g., capsules, tablets, powder, etc.), and the like. Most probiotics contain lactic acid bacteria, such as Lactobacilli and Bifidobacteria.

There is a need for further compositions, such as probiotics, which are suitable for maintaining, restoring and/or improving GI health in general, and/or for preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, encephalopathy, or others. There is also a need for beneficial GI bacteria that are capable of metabolizing or degrading fructose-lysine to prevent or reduce formation of AGEs.

BRIEF SUMMARY

In a first aspect, this disclosure provides an isolated intestinal bacterial strain, i.e., a human intestinal isolate, comprising a lysine pathway gene set, the bacterium being capable of converting L-lysine into butyric acid and/or butyrate or a derivative thereof, or a strain which has been derived therefrom.

In an embodiment, the lysine pathway gene set comprises one or more of the genes encoding the proteins: Lysine 2,3-aminomutase; L-beta-lysine 5,6-aminomutase alpha subunit; L-beta-lysine 5,6-aminomutase beta subunit; 3,5-diaminohexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase.

In an embodiment, the expression of at least one of the genes encoding the proteins: Lysine 2,3-aminomutase; L-beta-lysine 5,6-aminomutase alpha subunit; L-beta-lysine 5,6-aminomutase beta subunit; 3,5-diaminohexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase, is upregulated when the bacterium is grown on L-lysine as the sole carbon source as compared to when the bacterium is grown on equimolar amounts of glucose and acetate as the sole carbon source.

In an embodiment, at least one of the proteins: Lysine 2,3-aminomutase; L-beta-lysine 5,6-aminomutase alpha subunit; L-beta-lysine 5,6-aminomutase beta subunit; 3,5-diaminohexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase, is overexpressed when the bacterium is grown on L-lysine as the sole carbon source as compared to when the bacterium is grown on equimolar amounts of glucose and acetate as the sole carbon source.

The disclosure also pertains to an isolated intestinal bacterial strain deposited as CBS 139326 or a strain that has been derived therefrom. The bacterial strain may be capable of converting L-lysine into butyric acid and/or butyrate or a derivative thereof. The bacterial strain may be capable of converting L-lysine into butyric acid and/or butyrate or a derivative thereof and acetate or a derivative thereof.

The bacterial strain taught herein may further comprise a glycated lysine uptake and degradation operon, and may be capable of converting glycated lysine into butyric acid and/or butyrate or a derivative thereof.

The glycated lysine may be fructose-lysine, and the glycated lysine uptake and degradation operon may be a fructose-lysine uptake and degradation operon.

In an embodiment, the fructose-lysine uptake and degradation operon comprises one or more of the genes encoding the proteins: fructose-lysine kinase; fructose-lysine 3-epimerase; fructosamine deglycase; ABC transporter periplasmic spermidine putrescine-binding protein PotD; spermidine putrescine ABC transporter permease component PotC; spermidine putrescine ABC transporter permease component PotB; and putrescine transport ATP-binding protein PotA.

In an embodiment, the expression of at least one of the genes encoding the proteins: fructose-lysine kinase; fructoselysine 3-epimerase; fructosamine deglycase; ABC transporter periplasmic spermidine putrescine-binding protein PotD; spermidine putrescine ABC transporter permease component PotC; spermidine putrescine ABC transporter permease component PotB; and putrescine transport ATP-binding protein PotA, is upregulated when the bacterium is grown on L-lysine as the sole carbon source as compared to when the bacterium is grown on equimolar amounts of glucose and acetate as the sole carbon source.

In an embodiment, at least one of the proteins: fructose-lysine kinase; fructoselysine 3-epimerase; fructosamine deglycase; ABC transporter periplasmic spermidine putrescine-binding protein PotD; spermidine putrescine ABC transporter permease component PotC; spermidine putrescine ABC transporter permease component PotB; and putrescine transport ATP-binding protein PotA, is overexpressed when the bacterium is grown on L-lysine as the sole carbon source as compared to when the bacterium is grown on equimolar amounts of glucose and acetate as the sole carbon source.

The bacterial strain taught herein may belong to the phylum Firmicutes, the taxon *Clostridium* cluster IV, the genus Intestinimonas, and preferably belongs to the species Intestinimonas butyriciproducens.

In an embodiment, the bacterial strain taught herein is isolated from a human intestine, i.e., is a human intestinal isolate.

Preferably, the human intestinal isolate has an MIC of erythromycin of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml.

The disclosure further relates to a composition comprising a bacterial strain as taught herein and a physiologically acceptable carrier. The composition may be a food, food supplement, feed, feed supplement, or pharmaceutical composition.

In an embodiment, the composition taught herein is a food composition, such as a dairy product, e.g., a fermented dairy product, such as a yogurt or a yogurt drink.

In an embodiment, the composition taught herein is a pharmaceutical composition or a food supplement composition. The composition may be in solid dosage form, e.g., may be a capsule, a tablet, or a powder. The bacteria belonging to the bacterial strain taught herein may be incorporated into the composition in lyophilized form.

The bacterium may be present in the composition in an amount of about $10^2$ to about $10^{12}$, preferably $10^6$ to about $10^{10}$, colony forming units (CFU).

The composition may further comprise ingredients selected from the group consisting of prebiotics, probiotics, carbohydrates, polypeptides, lipids, vitamins, minerals, medicinal agents, preservative agents, or any combination thereof.

The composition may further comprise a lysine-rich source.

The disclosure also pertains to a bacterial strain as taught herein for use as a medicament, as well as to a composition as taught herein for use as a medicament.

Additionally, the disclosure relates to a bacterial strain as taught herein for use as a probiotic and/or symbiotic, as well as to a composition as taught herein for use as a probiotic and/or symbiotic.

In another aspect, this disclosure is concerned with a bacterial strain as taught herein or a composition as taught herein for use in maintaining, restoring and/or improving GI health in general, and/or for preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, or encephalopathy.

In a further aspect, this disclosure provides for a method for maintaining, restoring and/or improving GI health in general, and/or for preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, or encephalopathy in a subject in need thereof, the method comprising the step of increasing the level of a bacterial strain as taught herein in the subject.

In an embodiment, the level of the bacterial strain as taught herein may be increased in the subject by a method selected from the group consisting of administering an effective amount of the bacterial strain to the subject, and administering an effective amount of a compound capable of increasing the level of the bacterial strain in the subject.

In yet another aspect, the disclosure pertains to a method for preventing and/or reducing the production of glycated lysine in a subject comprising the step of increasing the level of a bacterial strain as taught herein in the subject.

In an embodiment, the level of the bacterial strain as taught herein may be increased in the subject by a method selected from the group consisting of administering an effective amount of the bacterial strain to the subject, and administering an effective amount of a compound capable of increasing the level of the bacterial strain in the subject.

Preferably, the subject is a mammal, even more preferably a human being.

General Definitions

The term "probiotics" or "probiotic products" as used herein refers to microorganisms such as intestinal bacteria, which—when administered or ingested in effective amounts—confer health benefits to the host (e.g., humans or mammals). Preferably, probiotics should be alive or viable when administered to a subject so as to allow the probiotics to colonize the large intestine of the host. However, under certain conditions, probiotics may also be dead when administered provided that substances produced by the probiotics still exert probiotic, beneficial effects on the host. Most probiotics or probiotic products are composed of lactic acid bacteria such as Lactobacilli or Bifidobacteria. The skilled person is well-acquainted with the field of probiotics and knows how to select lactic acid bacteria endowed with probiotic activity.

The term "prebiotics" or "prebiotic products" as used herein generally refers to compounds that promote the growth and/or activity of GI microorganisms that contribute to the well-being of their host. Prebiotics or prebiotic products consist mainly of fermentable fibers or non-digestible carbohydrates. The fermentation of these fibers by probiotics promotes the production of beneficial end products, such as SCFAs, particularly butyrates. The skilled person is well-acquainted with the field of prebiotics and knows how to select ingredients endowed with prebiotic activity.

The term "symbiotics" or "symbiotic products" as used herein generally refers to compositions and/or nutritional supplements combining probiotics and one or more compounds that promote the growth and/or activity of GI microorganisms, such as prebiotics, into one product. The symbiotic beneficially affects the host by improving the survival and colonization of the probiotic in the GI tract, by selectively stimulating the growth and/or by activating the metabolism of the probiotic, thus improving host welfare. The skilled person is well-acquainted with symbiotics and knows how to select ingredients that may be combined into a symbiotic.

The term "short chain fatty acids" (abbreviated as "SCFAs") as used herein refers to fatty acids with aliphatic tails of up to six carbons, including formic acid, acetic acid, propionic acid butyric acid and valeric acid (pentanoic acid), while branched chain fatty acids (BCFAs) include isobutyric acid (2-methylpropanoic acid) and isovaleric acid (3-methylbutanoic acid), and the like. SCFAs may be produced when dietary fibers are fermented in the lower intestine of mammals while BCFAs are predominantly formed from protein fermentation. Specifically, the production of the SCFAs acetic acid, propionic acid and butyric acid in the lower intestine of mammals is the result of fermentation of dietary carbohydrates.

The term "butyric acid" (also known under the systematic name butanoic acid) as used herein refers to a carboxylic acid with the structural formula $CH_3CH_2CH_2COOH$. The term "butyric acid or a derivative thereof" as used herein refers to compounds derived from butyric acid and includes salts and esters of butyric acid, which are known as butyrates or butanoates. Non-limiting examples of butyrate salts include sodium butyrate, calcium butyrate, magnesium butyrate, manganese butyrate, cobalt butyrate, barium butyrate, lithium butyrate, zinc butyrate, potassium butyrate, ferrous butyrate and the like. Non-limiting examples of butyrate esters (i.e., esters of butyric acid) include cellulose acetate butyrate, methyl butyrate, ethyl butyrate, butyl butyrate, pentyl butyrate, and the like.

The terms "butyrate-producing bacterium" or "butyric acid-producing bacterium" or "butyrogenic bacterium" are used interchangeably herein and refer to a bacterium which is capable of producing butyric acid and/or butyrate and/or one or more derivatives thereof. A prominent pathway by which butyric acid and/or butyrate and derivative thereof may be produced in situ in the mammalian gut (or in vitro in culture) is the so-called "acetyl-CoA pathway." The acetyl-CoA pathway has been well-documented and is known to be particularly prevalent in intestinal bacteria belonging, for instance, to the genus Lachnospiraceae and Ruminococcaceae (which together may form up to 20% of total gut microbiota). According to the acetyl-CoA pathway, butyric acid and/or butyrate and/or derivatives thereof may be formed by a single bacterial species via carbohydrate fermentation and/or by a group of microorganisms where metabolites from other organisms act as a substrate for butyrogenic bacteria. The conventional acetyl-CoA pathway involves a cascade of enzymes, including (among many others) two key enzymes referred to as butyryl-CoA transferase (But) and butyrate kinase (Buk). The skilled person is well-acquainted with the acetyl-CoA pathway including genes coding for enzymes and other elements underlying the functioning of the pathway as well as intestinal bacterial species that have this pathway.

It has been hypothesized that other pathways by which butyric acid and/or butyrate and/or derivatives thereof may be produced in the human GI may exist. One of such pathways is the so-called "lysine utilization pathway" or "lysine pathway." However, this pathway has not been reported to exist in bacterial species isolated from the human GI (Vital et al., 2014, mBio 5(2) doi:10.1128/mBio.00889-14).

The term "lysine pathway gene set" as used herein refers to a set of genes that encode proteins involved in the lysine pathway for conversion of L-Lysine into butyric acid and/or butyrates or a derivative thereof. In an embodiment of this disclosure, the lysine pathway gene set comprises genes encoding the proteins: Lysine 2,3-aminomutase; L-beta-lysine 5,6-aminomutase alpha subunit; L-beta-lysine 5,6-aminomutase beta subunit; 3,5-diaminohexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase. The lysine pathway gene set may further comprise one or more genes encoding the proteins: L-Lysine permease; butyryl-CoA dehydrogenase Etf; 4-hydroxybutyrate coenzyme A transferase; 3-ketoacyl-CoA thiolase/acetyl-CoA acetyltransferase; phosphate acetyltransferase; acetate kinase; proton pumping Rnf cluster (A, B, C, D, E, G subunits); V-type ATP synthase cluster (A, B, C, D, E, F, I, K subunits); inorganic pyrophosphatase; ammonium transporter; putative short chain fatty acids transporter; and Na+/H+ antiporter.

In an embodiment of this disclosure, the lysine pathway gene set may further comprise one or more genes encoding the proteins: 3-hydroxybutyryl-CoA dehydratase; D-beta-hydroxybutyrate permease; electron transfer flavoprotein alpha subunit; electron transfer flavoprotein beta subunit; NAD-reducing hydrogenase subunit HoxE; ferredoxin; NAD-reducing hydrogenase subunit HoxF; periplasmic [Fe] hydrogenase large subunit; and Substrate-specific component RibU of riboflavin ECF transporter.

The term "lysine" as used in the context of this disclosure advantageously refers to "L-lysine," and can be used interchangeably.

The term "fructose-lysine uptake and degradation operon" or "glycated lysine uptake and degradation operon" as used herein refers to a set of genes involved in the fructose-lysine uptake and degradation pathway for converting fructose-lysine into butyric acid and/or butyrate or a derivate thereof.

In an embodiment, the "fructose-lysine uptake and degradation operon" comprises genes coding for the proteins: fructose-lysine kinase; fructose-lysine 3-epimerase; fructosamine deglycase; and an ABC transporter consisting of 4 subunits, the periplasmic spermidine putrescine-binding protein PotD, the spermidine putrescine ABC transporter permease component PotC, the spermidine putrescine ABC transporter permease component PotB, and the putrescine transport ATP-binding protein PotA.

The term "beneficial intestinal bacteria species" as used herein refers to a bacterium species that inhabits (i.e., is innate) the mammalian (e.g., human) intestine and exerts beneficial effect(s) (e.g., protection against pathogenic bacteria species, production of butyric acid and/or butyrate and derivatives, etc.) on the GI, metabolic and other health of a mammal in which it resides.

Non-limiting examples of beneficial intestinal bacterial species include lactic acid bacteria from the genera *Lactobacillus* and *Bifidobacterium*. Other non-limiting examples of beneficial intestinal bacterial species include butyrate-producing bacterial species, which use the acetyl-CoA to produce butyric acid and/or butyrate and derivatives thereof, such as the bacterial strains disclosed in US 2014/0242654, WO 2014/150094 or WO 2013032328 A1.

The term "pathogenic bacterial species" as used herein refers to a bacterium that inhabits (i.e., is innate) the mammalian (e.g., human) intestine and exerts deleterious effect(s) (e.g., infection) on the GI health of a mammal in which it resides. A notorious non-limiting example of a pathogenic bacterial species is the toxin-producing *Clostridium difficile*.

The term "glycated lysine" or "Amadori glycated lysine" or "fructose-lysine" as used herein refers to a product comprising a lysine in which a lysine epsilon $NH_2$ group is glycated by means of an Amadori rearrangement. The skilled person is well-acquainted with the process by which Amadori glycated lysine or fructose-lysine are formed. The term fructose-lysine is employed when a glucose moiety is covalently coupled to a lysine via an Amadori arrangement. Fructose-lysine is also known as ε-fructose-lysine, 1-Deoxy-1-(ε-N-L-lysino)-D-fructose; fructosyllysine; Nε-(1-Deoxy-D-fructos-1-yl)-L-lysine; D-1-[(L-5-Amino-5-carboxypentyl)amino]-1-deoxyfructose; or (S)-1-[(5-Amino-5-carboxypentyl)amino]-1-deoxy-D-Fructose.

Amadori glycated lysine and fructose-lysine are abundant in cooked foods. Amadori glycated lysine or fructose-lysine are typically formed via non-enzymatic reaction of glucose and amino acids upon the food heating process. Spontaneous chemical conversion under slight alkaline conditions can result in further rearrangement, fragmentation and oxidation reactions of FL, resulting in the formation of well-known AGEs, such as $N^ε$-(carboxymethyl)lysine. AGEs have been implicated in a variety of diseases, such as metabolic syndrome, type 2 diabetes mellitus, cardiovascular disease, ovarian aging, polycystic ovary syndrome and neurodegenerative disorders, such as Alzheimer's disease, multiple sclerosis and dementia.

The term "effective amount" as used herein refers to an amount necessary to achieve an effect as taught herein. For instance, an effective amount of the intestinal bacterial strain or a strain derived therefrom as taught herein is an amount which is effectively useful for maintaining, restoring, and/or improving GI heath in a human being, for converting Amadori glycated lysine or fructose-lysine into butyric acid and/or butyrate or a derivative thereof and/or for preventing and/or treating conditions or diseases described herein, which are related to the presence of lysine, the absence or reduction of butyrogenic GI bacteria, or to the presence of AGEs, in a subject, preferably a human being. These conditions or diseases include, without limitation, cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, or encephalopathy. The effective amount can be readily determined without undue experimentation by a person of ordinary skill in the art.

The term "a strain that derives therefrom" as used herein relates to strains obtained by using the deposited strain as taught herein as starting material. The strain that derives therefrom may be a mutant strain, which may be derived from a strain of the disclosure by means of, for instance, genetic engineering, radiation, UV light, chemical treatment. Alternatively, such derivative or mutant strain may be a strain derived from the deposited strain as taught herein that has been subjected to growth adaptation to particular conditions resulting in an additional benefit to the derivative strain, such as more rapid growth, better survival in the gut, enhanced lysine to butyrate conversion and/or enhanced glycated lysine, e.g., fructose-lysine, to butyrate conversion due to adaptation to growth on lysine and/or glycated lysine, e.g., fructose-lysine, and the like, using methods that are well-known to the skilled person. It is preferred that the derivative or mutant is functionally equivalent to the deposited strain as taught herein. A preferred derivative or mutant as taught herein has substantially the same activity or function as the deposited strain as taught herein, i.e., has the ability to convert L-lysine into butyric acid and/or butyrate and derivatives and/or has the ability to convert glycated lysine, e.g., fructose-lysine, into butyric acid and/or butyrate or a derivative thereof. The derivative or mutant advantageously provides substantially the same benefits to a mammal (e.g., humans or other mammals) administered with the derivative or mutant as would be the case upon administration of the deposited strain. The derivative or mutant strain may also be a spontaneous derivative or mutant strain having the same characteristics as described herein for the deposited strain.

The term "suitable for consumption" or "nutritionally acceptable" refers to ingredients or substances, which are generally regarded as safe for human (as well as other mammals) consumption.

"Minimum inhibitory concentration" or "MIC" as used herein refers to the lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. An MIC is generally regarded as the most basic laboratory measurement of the activity of an antimicrobial agent against an organism.

The term "about," as used herein, indicates a range of normal tolerance in the art, for example within two standard deviations of the mean. The term "about" can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms "comprising" or "to comprise" and their conjugations, as used herein, refer to a situation wherein the terms are used in their non-limiting sense to mean that items following the word are included, but items not specifically mentioned are not excluded. It also encompasses the more limiting verb "to consist essentially of" and "to consist of."

Reference to an element by the indefinite article "a" or "an" does not exclude the possibility that more than one of the elements is present, unless the context clearly requires that there be one and only one of the elements. The indefinite article "a" or "an" thus usually means "at least one."

The terms "to increase" and "increased level" and the terms "to decrease" and "decreased level" refer to the ability to significantly increase or significantly decrease or to a significantly increased level or significantly decreased level. Generally, a level is increased or decreased when it is at least 5%, such as 10%, 15%, 20%, 25%, 30%, 35%, 40%, 45%, 50% higher or lower, respectively, than the corresponding level in a control or reference. Alternatively, a level in a sample may be increased or decreased when it is statistically significantly increased or decreased compared to a level in a control or reference.

DETAILED DESCRIPTION

The present inventors have isolated for the first time a new intestinal bacterial strain from the human GI tract, which is referred to herein as Intestinimonas AF211. Specifically, the new intestinal bacterial strain is a butyric acid and/or butyrate-producing (butyrogenic) bacterium, which is capable of converting L-lysine into butyric acid and/or butyrate or a derivative thereof via the so-called "lysine utilization pathway." The new intestinal bacterial strain of the disclosure is further capable of converting a glycated lysine or other AGEs, e.g., fructose-lysine, into butyric acid and/or butyrate or a derivative thereof via the so-called "fructose-lysine uptake and degradation pathway."

Without wishing to be bound to any theories, it is believed that the novel intestinal bacterial strain (or strains derived therefrom) taught herein, when administered to a human being or when ingested by a human being in an adequate amount, is able to colonize the GI tract of the human being. This colonization enables greater in situ production of butyric acid and/or butyrate or a derivative thereof as well as greater metabolism of fructose-lysine or other glycated lysine in the GI tract of the human being. Increased in situ production of butyric acid and/or butyrate or a derivative thereof and/or increased metabolism of fructose-lysine in the GI tract is believed to underlie the beneficial effects as taught herein, e.g., maintaining, restoring and/or improving GI health in general, and/or preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome and neurodegenerative disorders, such as Alzheimer's disease, multiple sclerosis and dementia, or others.

Bacterium

In a first aspect, this disclosure relates to a bacterial strain, or a strain derived therefrom, that comprises a lysine pathway gene set and is capable of converting L-lysine into butyric acid and/or butyrate or a derivative thereof. The bacterial strain is preferably a human intestine isolate.

In a second aspect, this disclosure relates to a bacterial strain deposited by Wageningen University on Jan. 5, 2015 at the Centraalbureau voor Schimmelcultures located in Utrecht, the Netherlands, assigned the deposit number CBS 139326.

In an embodiment, the isolated bacterium as taught herein may be further capable of converting L-Lysine into butyric acid and/or butyrate or a derivative thereof and acetate or a derivative thereof. Acetate is thought to reduce the appetite and may therefore be useful for weight loss purposes, e.g., for treating and/or preventing obesity.

In an embodiment, the intestinal bacterial strain as taught herein may be capable of converting L-lysine into butyric acid and/or butyrate or a derivative thereof from any protein sources comprising lysine. Non-limiting examples of protein sources comprising lysine include tryptic soy broth without dextrose, trypton, casiton, vegetable peptone, yeast extract, bacterial peptone, casein hydrolysate, methyllysine, and the like.

In an embodiment, the lysine pathway gene set may comprise one or more of the genes encoding the proteins: lysine 2,3-aminomutase; L-beta-lysine 5,6-aminomutase alpha subunit; L-beta-lysine 5,6-aminomutase beta subunit; 3,5-diaminobexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase. Alternatively, the lysine pathway gene set may comprises at least two, three, four, five, six, seven, eight or all nine of the genes encoding the proteins: lysine 2,3-aminomutase; L-beta-lysine 5,6-aminomutase alpha subunit; L-beta-lysine 5,6-aminomutase beta subunit; 3,5-diaminobexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase.

The lysine pathway gene set may further comprise one or more of the genes encoding the proteins: L-Lysine permease; butyryl-CoA dehydrogenase Etf; 4-hydroxybutyrate coenzyme A transferase; 3-ketoacyl-CoA thiolase/acetyl-CoA acetyltransferase; phosphate acetyltransferase; acetate kinase; proton pumping Rnf cluster (A, B, C, D, E, G subunits); V-type ATP synthase cluster (A, B, C, D, E, F, I, K subunits); inorganic pyrophosphatase; ammonium transporter; putative short chain fatty acids transporter; and Na+/H+ antiporter. Additionally, the "lysine pathway gene set" may further comprise one or more genes encoding the proteins: 3-hydroxybutyryl-CoA dehydratase; D-beta-hydroxybutyrate permease; electron transfer flavoprotein alpha subunit; electron transfer flavoprotein beta subunit; NAD-reducing hydrogenase subunit HoxE; ferredoxin; NAD-reducing hydrogenase subunit HoxF; periplasmic [Fe] hydrogenase large subunit; and Substrate-specific component RibU of riboflavin ECF transporter. In an embodiment, the expression of one or more genes encoding proteins: lysine 2,3-aminomutase; L-beta-lysine 5,6-aminomutase alpha subunit; L-beta-lysine 5,6-aminomutase beta subunit; 3,5-diaminobexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase, may be upregulated when the bacterium is grown on L-lysine as the sole carbon source as compared to when the bacterium is grown on equimolar amounts of glucose and acetate as the sole carbon source.

In an embodiment, at least one of the proteins: lysine 2,3-aminomutase; L-beta-lysine 5,6-aminomutase alpha subunit; L-beta-lysine 5,6-aminomutase beta subunit; 3,5-diaminobexanoate dehydrogenase; 3-keto-5-aminohexanoate cleavage enzyme; 3-aminobutyryl-CoA ammonia-lyase; butyrate-acetoacetate CoA-transferase subunit A; butyrate-acetoacetate CoA-transferase subunit B; acetyl-CoA:acetoacetyl-CoA transferase, may be overexpressed when the bacterium is grown on L-lysine as the sole carbon source as compared to when the bacterium is grown on equimolar amounts of glucose and acetate as the sole carbon source.

In the context of this disclosure, the amount of L-lysine used to determine whether genes are upregulated or proteins are overexpressed in a bacterial strain as compared to when the bacterium is grown on equimolar amounts of glucose and acetate may be in the range of from about 5 mM to about 100 mM, preferably from about 10 mM to about 50 mM, more preferably from about 15 mM to about 25 mM, and is most preferably about 20 mM (particularly when the comparative experiments of the bacterial strain being grown on equimolar amounts of glucose and acetate as the sole carbon source is carried out in 40 mM glucose and 40 mM acetate).

In the context of this disclosure, the equimolar amounts of glucose and acetate referred to herein may be in the range of from about 1 mM to about 200 mM of both glucose and acetate, which may be provided in the form of an acetate salt such as sodium acetate, preferably from about 5 mM to about 150 mM of both glucose and acetate, more preferably form about 10 mM to about 100 mM of both glucose and acetate, even more preferably from about 15 mM to about 75 mM of both glucose and acetate, yet more preferably from about 20 mM to about 60 mM of both glucose and acetate, such as from about 25 mM to about 55 mM of both glucose and acetate, from about 30 mM to about 50 mM of both glucose and acetate, from about 35 mM to about 50 mM of both glucose and acetate, preferably about 40 mM of both glucose and acetate.

In an embodiment, the isolated intestinal bacterial strain, or a strain derived therefrom as taught herein further comprises a glycated lysine uptake and degradation operon.

In an embodiment, the isolated intestinal bacterial strain, or strain derived therefrom, as taught herein is further capable of converting a glycated lysine into butyric acid and/or butyrate or a derivative thereof.

In an embodiment, the glycated lysine is fructose-lysine and the glycated lysine uptake and degradation operon is a fructose-lysine uptake and degradation operon.

In an embodiment, the fructose-lysine uptake and degradation operon comprises one or more of the genes encoding the proteins: fructose-lysine kinase; fructoselysine 3-epimerase; fructosamine deglycase; and the ABC transporter consisting of the 4 subunits: ABC transporter periplasmic spermidine putrescine-binding protein PotD; spermidine putrescine ABC transporter permease component PotC; spermidine putrescine ABC transporter permease component PotB; and putrescine transport ATP-binding protein PotA. For example, the fructose-lysine uptake and degradation operon may comprise at least two, three, four, five, six or all seven of the genes encoding the proteins: fructose-lysine kinase; fructoselysine 3-epimerase; fructosamine deglycase; and the ABC transporter consisting of the 4 subunits: ABC transporter periplasmic spermidine putrescine-binding protein PotD; spermidine putrescine ABC transporter permease component PotC; spermidine putrescine ABC transporter permease component PotB; and putrescine transport ATP-binding protein PotA.

In an embodiment, the expression of at least one of the genes encoding the proteins: fructose-lysine kinase; fructoselysine 3-epimerase; fructosamine deglycase; ABC transporter periplasmic spermidine putrescine-binding protein PotD; spermidine putrescine ABC transporter permease component PotC; spermidine putrescine ABC transporter permease component PotB; and putrescine transport ATP-binding protein PotA, is upregulated when the bacterium is grown on L-lysine as the sole carbon source as compared to when the bacterium is grown on equimolar amounts of glucose and acetate as the sole carbon source.

In another embodiment, at least one of the proteins: fructose-lysine kinase; fructoselysine 3-epimerase; fructosamine deglycase; ABC transporter periplasmic spermidine putrescine-binding protein PotD; spermidine putrescine ABC transporter permease component PotC; spermidine ABC transporter permease component PotB; and putrescine transport ATP-binding protein PotA, is overexpressed when the bacterium is grown on L-lysine as the sole carbon source as compared to when the bacterium is grown on equimolar amounts of glucose and acetate as the sole carbon source.

In the context of this disclosure, the amount of L-lysine used to determine whether genes are upregulated or proteins are overexpressed in a bacterial strain as compared to when the bacterium is grown on equimolar amounts of glucose and acetate may be in the range of from about 5 mM to about 100 mM, preferably from about 10 mM to about 50 mM, more preferably from about 15 mM to about 25 mM, and is most preferably about 20 mM (particularly when the comparative experiments of the bacterial strain being grown on equimolar amounts of glucose and acetate as the sole carbon source is carried out in 40 mM glucose and 40 mM acetate).

In the context of this disclosure, the equimolar amounts of glucose and acetate referred to herein may be in the range of from about 1 mM to about 200 mM of both glucose and acetate, which may be provided in the form of an acetate salt such as sodium acetate, preferably from about 5 mM to about 150 mM of both glucose and acetate, more preferably form about 10 mM to about 100 mM of both glucose and acetate, even more preferably from about 15 mM to about 75 mM of both glucose and acetate, yet more preferably from about 20 mM to about 60 mM of both glucose and acetate, such as from about 25 mM to about 55 mM of both glucose and acetate, from about 30 mM to about 50 mM of both glucose and acetate, from about 35 mM to about 50 mM of both glucose and acetate, preferably about 40 mM of both glucose and acetate.

In an embodiment, the isolated human intestinal bacterial strain, or strain derived therefrom, as taught herein comprises the lysine pathway gene set as taught herein and/or the fructose-lysine uptake and degradation operon as taught herein.

In a preferred embodiment, the isolated human intestinal bacterial strain, or strain derived therefrom, as taught herein comprises both the lysine pathway gene set as taught herein and the fructose-lysine uptake and degradation operon as taught herein.

In an embodiment, the isolated intestinal bacterial strain, or strain derived therefrom, as taught herein is an intestinal bacterium isolated from a human being, which naturally comprises a lysine pathway gene set and/or a fructose-lysine uptake and degradation operon as taught herein and which is capable of converting L-lysine into butyric acid and/or butyrate or a derivative thereof and/or is capable of converting fructose-lysine into butyric acid and/or butyrate or a derivative thereof.

In another embodiment, the bacterial strain as taught herein is a bacterial strain, which has been transfected with the lysine pathway gene set and/or the fructose-lysine uptake and degradation operon as taught herein, and which is capable of converting L-lysine into butyric acid and/or butyrate or a derivative thereof and/or is capable of converting fructose-lysine into butyric acid and/or butyrate or a derivative thereof. The skilled person is well-acquainted with methods for transfecting bacteria with a desired genetic construct (e.g., operon or pathway gene set).

Preferably, the human intestinal isolate taught herein is sensitive to erythromycin, having an MIC of erythromycin of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml. This allows the isolate to be administered to human beings without introducing erythromycin-resistant bacteria.

In an embodiment, the human intestinal isolate taught herein is sensitive to cefotaxime, having an MIC of cefotaxime of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml, even more preferably less than 1 µg/ml. This allows the isolate to be administered to human beings without introducing cefotaxime-resistant bacteria.

In an embodiment, the human intestinal isolate taught herein is sensitive to oxacillin, having an MIC of oxacillin of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml, even more preferably less than 1 µg/ml. This allows the isolate to be administered to human beings without introducing oxacillin-resistant bacteria.

In an embodiment, the human intestinal isolate taught herein is sensitive to teicoplanin, having an MIC of teicoplanin of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml, even more preferably less than 1 µg/ml. This allows the isolate to be administered to human beings without introducing teicoplanin-resistant bacteria.

In an embodiment, the human intestinal isolate taught herein is sensitive to tobramycin, having an MIC of tobramycin of less than 20 µg/ml, more preferably less than 15 µg/ml, yet more preferably less than 10 µg/ml, yet more preferably less than 7 µg/ml, even more preferably less than 5 µg/ml, most preferably less than 4, or less than 3. This allows the isolate to be administered to human beings without introducing tobramycin-resistant bacteria.

In an embodiment, the human intestinal isolate taught herein is sensitive to vancomycin, having an MIC of vancomycin of less than 20 µg/ml, more preferably less than 15 µg/ml, yet more preferably less than 10 µg/ml, yet more preferably less than 7 µg/ml, even more preferably less than 5 µg/ml, most preferably less than 4, less than 3, or less than 2 µg/ml, even more preferably less than 1 µg/ml. This allows the isolate to be administered to human beings without introducing vancomycin-resistant bacteria.

In an embodiment, the isolate taught herein is sensitive to all of cefotaxime, erythromycin, oxacillin, teicoplanin, tobramycin and vancomycin.

In an embodiment, the isolated intestinal bacterial strain, or a strain derived therefrom as taught herein belongs to the phylum Firmicutes, preferably to the taxon Clostridium cluster IV (Ruminococcacaea; Rajilic-Stojanovic & De Vos 2014, FEMS Microbiol. Rev. 38:996-1047), more preferably to the genus Intestinimonas, even more preferably to the species Intestinimonas butyriciproducens.

Kläring et al. (2013, Int. J. of Syst. and Evol. Microbiol. 63:4606) disclose a mouse intestinal isolate designated Intestinimonas butyriciproducens strain SRB-521-54 (deposited as DSM 26588). Mouse intestinal isolates are unsuitable for administration to humans. Particularly, it was found that, while both strains were capable of producing butyrate from sugars and lysine, the human strain AF211 was more efficient in these conversions than the mouse isolate. Notably, this was observed with arabinose and galactose, two sugars found abundantly in the human but not mouse diet (unpublished data).

Pfleiderer et al. (2013, Eur. J. Clin. Microbiol. Infect. Dis. 32:1471) describe new bacterial species, one of which is designated Clostridium anorexicus strain AP4, which now has been reclassified as "Intestinimonas butyriciproducens strain AP4" based on the 16S rRNA sequence. This strain is not publicly available, and has not been described in detail.

In an embodiment, the isolated bacterial strain, or strain derived therefrom, as taught herein is not Intestinimonas butyriciproducens strain ER1, and/or Intestinimonas butyriciproducens strain SRB-521-5-I (DSM 26588; a mouse intestinal isolate), and/or Clostridium anorexicus strain AP4 (also referred to as "Intestinimonas butyriciproducens strain AP4").

Compositions

In a third aspect, this disclosure relates to a composition comprising any of the isolated bacterial strains, or strains derived therefrom, as taught herein and a physiologically acceptable carrier.

In an embodiment, the isolated bacterial strain, or strain derived therefrom, as taught herein is not Intestinimonas butyriciproducens strain ER1, and/or Intestinimonas butyriciproducens strain SRB-521-5-I (DSM 26588), and/or Clostridium anorexicus strain AP4.

In a preferred embodiment, the composition as taught herein comprises the isolated intestinal bacterial strain deposited as CBS 139326 (also referred to as "Intestinimonas AF211"), or a strain derived therefrom, and a physiologically acceptable carrier.

In an embodiment, the physiologically acceptable carrier may be any carrier that is suitable for keeping the intestinal bacterial strain as taught herein viable until consumption by a subject (e.g., humans and/or animals). For instance, non-limiting examples of acceptable carriers that are suitable for this purpose include any of well-known physiological or pharmaceutical carriers, buffers, and excipients. It will be appreciated that the choice for a suitable physiological or pharmaceutical carrier will depend upon the intended mode of administration of the composition as taught herein (e.g., oral) and the intended form of the composition (e.g., beverage, yogurt, powder, capsules, and the like). The skilled person knows how to select a physiological or pharmaceutical carrier, which is suitable for the compositions as taught herein.

In an embodiment, the composition as taught herein may be in the form of a food composition, feed composition, feed supplement composition, food supplement composition or pharmaceutical composition. The composition is preferably suitable for consumption by a human being.

In an embodiment, the composition is a food or food supplement composition. The food or food supplement composition may be selected from the group consisting of a liquid, liquid beverage (including dairy beverage and fermented beverage), yogurt, cheese, gel, gelatin, gelatin capsule, powder, paste, pressed tablet, and gel cap. In a suitable embodiment, the composition is a liquid, preferably a liquid beverage (e.g., dairy beverage). The food or food supplement composition may be a dairy product, preferably a fermented dairy product, preferably a yogurt or a yogurt drink.

In an embodiment, the composition as taught herein may be a probiotic composition. Such probiotic composition may comprise any of the isolated intestinal bacterial strain as taught herein, or a strain derived therefrom.

In an embodiment, the composition as taught herein further comprises one or more additional beneficial isolated intestinal bacterial strain.

In one embodiment, the one or more additional beneficial isolated intestinal bacterial strain may be any lactic acid bacterial strain selected from the genera Lactobacillus and/ or *Bifidobacterium* and/or any butyrate-producing bacteria which produces butyrate via the acetyl-CoA pathway.

In an embodiment, the composition may be a symbiotic composition. It may be advantageous to add one or more prebiotic ingredients to the composition as taught herein, for example, to enhance the effects (e.g., production of butyric acid and/or butyrate or a derivative thereof) of the intestinal bacterial strain as taught herein.

In an embodiment, the one or more prebiotic ingredients may be any prebiotic ingredients, which are suitable to enhance the activity and/or stimulate the growth of the isolated intestinal bacterium, or a strain derived therefrom, as taught herein. Non-limiting examples of suitable prebiotic ingredients include fibers, cellobiose, maltose, mannose, salicine, trehalose, amygdalin, arabinose, melibiose, rhamnose and/or xylose.

In an embodiment, the composition as taught herein comprises a lysine-rich source and/or lysine. For instance, it may be advantageous to add a lysine rich source and/or lysine to the composition as taught herein to further promote the production of butyric acid and/or butyrate or a derivative thereof in the GI tract of a mammal (e.g., human being).

In an embodiment, the composition as taught herein may comprise one or more ingredients which are suitable for promoting survival and/or viability of the isolated intestinal bacterial strain or strain derived therefrom as taught herein during storage and/or during exposure to bile and/or during passage through the GI tract of a mammal (e.g., a human being). Non-limiting examples of such ingredients include an enteric coating, and controlled release agents allowing passage through the stomach. The skilled person knows how to select suitable ingredients for maintaining an isolated intestinal bacterial strain (such as any of the isolated intestinal bacterium as taught herein) viable and functional, i.e., able to carry out their intended function(s).

In one embodiment, the compositions as taught herein may further comprise one or more ingredients, which further enhance the nutritional value and/or the therapeutic value of the compositions as taught herein. For instance, it may be advantageous to add one or more ingredients (e.g., nutritional ingredients, veterinary or medicinal agents, etc.) selected from proteins, amino acids, enzymes, mineral salts, vitamins (e.g., thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g., water-soluble and water-insoluble monosaccharides, disaccharides, and polysaccharides), medicinal compounds (e.g., antibiotics), antioxidants, trace element ingredients (e.g., compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value of the compositions as taught herein.

The bacterial strain taught herein may be incorporated into the composition in lyophilized form, microencapsulated form (reviewed by, for example, Solanki et al., *BioMed. Res. Int.* 2013, Article ID 620719), or any other form preserving the activity and/or viability of the bacterial strain.

The composition as taught herein may be a pharmaceutical composition. The pharmaceutical composition may be for use as a supplement. A pharmaceutical composition will usually comprise a pharmaceutical carrier, in addition to the bacterial strain taught herein. The carrier is preferably an inert carrier. The preferred form depends on the intended mode of administration and (therapeutic) application. A pharmaceutical carrier can be any compatible, nontoxic substance suitable to deliver bacteria of the bacterial strain taught herein to the GI tract of a subject. For example, sterile water, or inert solids may be used as a carrier, usually complemented with a pharmaceutically acceptable adjuvant, buffering agent, dispersing agent, and the like. A pharmaceutical composition as taught herein may be in liquid form, e.g., a stabilized suspension of bacteria of the bacterial strain taught herein, or in solid form, e.g., a powder of lyophilized bacteria of the bacterial strain taught herein. In case the bacterial strain taught herein is lyophilized, a cryoprotectant such as lactose, trehalose or glycogen can be employed. For example, for oral administration, bacteria of the bacterial strain taught herein can be administered in solid dosage forms, such as capsules, tablets, and powders, comprising lyophilized bacteria, or in liquid dosage forms, such as elixirs, syrups, and suspensions. Bacteria of the bacterial strain taught herein, e.g., in lyophilized form, can be encapsulated in capsules such as gelatin capsules, together with inactive ingredients and powdered carriers, such as, e.g., glucose, lactose, sucrose, mannitol, starch, cellulose or cellulose derivatives, magnesium stearate, stearic acid, sodium saccharin, talcum, magnesium carbonate and the like.

In an embodiment, the intestinal bacterium or strain derived therefrom as taught herein may be comprised in the composition as taught herein in an amount ranging from about $10^6$ to about $10^{15}$ colony forming units (CFU). For instance, the intestinal bacteria may be comprised in the composition in an amount of about $10^7$ CFU to about $10^{14}$ CFU, preferably about $10^8$ CFU to about $10^{13}$ CFU, preferably about $10^9$ CFU to about $10^{12}$ CFU, more preferably about $10^{10}$ CFU to about $10^{12}$ CFU.

The compositions as taught herein may be produced by any conventional methods.

Methods and Uses of the Invention

In another aspect, this disclosure is concerned with a bacterial strain as taught herein or a composition as taught herein for use as a medicament, for use as a food or food supplement, or for use as a probiotic and/or symbiotic.

In yet another aspect, the disclosure pertains to a bacterial strain as taught herein or a composition as taught herein for use in maintaining, restoring and/or improving GI health in general, and/or for preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, or encephalopathy.

The disclosure is also directed to a method for maintaining, restoring and/or improving GI health in general, and/or for preventing and/or treating conditions or diseases such as cancer (e.g., colorectal cancer), IBD (e.g., Crohn's disease, ulcerative colitis), IBS, obesity, bacterial and viral diarrhea, constipation, bloating, allergies, urinary tract infections, metabolic diseases, such as metabolic syndrome and insulin resistance or insulin resistance-related complications, such as dyslipidemia and type 2 diabetes mellitus as well as insulin-resistance in endocrine diseases (e.g., obese subjects with type 1 diabetes mellitus, Cushing's disease or lipodystrophy syndromes), cardiovascular disease, ovarian aging, polycystic ovary syndrome, neurodegenerative disorders, such as Alzheimer's disease, multiple sclerosis and dementia, or encephalopathy in a subject in need thereof, the method comprising the step of increasing the level of a bacterial strain as taught herein in the subject. The level of the bacterial strain as taught herein in the subject may be increased by administering an effective amount of the bacterial strain to the subject, and/or by administering an effective amount of a compound capable of increasing the level of the bacterial strain in (the GI tract of) the subject.

In a further aspect, this disclosure relates to methods for metabolizing fructose-lysine and/or for preventing and/or reducing the formation of glycated lysine, such as fructose-lysine or other AGEs, and/or for increasing levels of butyric acid and/or butyrate or a derivative thereof in the GI tract of a subject, the method comprising the step of increasing the level of the bacterial strain as taught herein in the GI tract of the subject.

In an embodiment, the level of the intestinal bacterial strain or a strain derived therefrom as taught herein in the GI tract of the subject may be increased either by administering an effective amount of the isolated intestinal bacterial strain to the subject, or by administering an effective amount of a compound capable of increasing the level of the intestinal bacterium in the GI tract of the subject.

The bacterial strain or a strain derived therefrom as taught herein may be administered in the form of a composition as taught herein.

In an embodiment, the bacterial strain or a strain derived therefrom as taught herein may be administered concomitant with lysine or a lysine-rich compound, such as proteins or protein fragments derived from bovine or other milks as well as plant origin such as soy, cowpea or other beans. The skilled person can, without undue burden, readily identify lysine-rich compounds.

In a preferred embodiment, the level of the bacterial strain or a strain derived therefrom as taught herein in the GI tract of a subject may be increased by administering an effective amount of the bacterial strain or a strain derived therefrom as taught herein and/or compositions as taught herein, but preferably Intestinimonas AF211 and/or a composition comprising Intestinimonas AF211, to the subject.

In an embodiment, the subject may be selected from the group consisting of human beings, non-human primates, mice, rats, dogs, cows, and pigs. In a preferred embodiment, the subject is a human. In a specific embodiment the subject is a human with a reduced amount of butyrogenic bacteria, specifically butyrogenic bacteria of the disclosure, in the GI tract.

The disclosure also relates to a method for producing butyrate, the method comprising the step of contacting the bacterial strain as taught herein with a suitable energy source, e.g., lysine or glucose/acetate, under conditions which allow the bacterial strain as taught herein to convert the energy source to butyrate.

Additionally, the disclosure relates to a method for producing butyrate, the method comprising the step of contacting the bacterial strain as taught herein with fructose-lysine under conditions which allow the bacterial strain to convert the fructose-lysine to butyrate.

The methods taught herein may be in vitro methods.

This disclosure is further illustrated, but not limited, by the following examples. From the above discussion and these examples, one skilled in the art can ascertain the essential characteristics of the disclosure, and without departing from the teaching and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

FIG. 1 shows lysine conversion and butyrate and acetate production upon growth of AF211 on L-lysine as the sole carbon source.

EXAMPLES

Example 1: Functional Analysis of Intestinimonas AF211

The goal of this study was to assess whether the strain Intestinimonas AF211 is capable of converting L-lysine into butyric acid and/or butyrate or a derivative thereof.

Culture:

A fecal sample from a healthy subject was collected. The fecal sample was enriched in an anaerobic bicarbonate buffered mineral salt medium containing 40 mM lactate and 40 mM acetate as an energy and carbon source. The headspace was filled with $CO^2/N^2$ (1:5) at 1.5 atm and incubated at 37° C. Subsequently the strain Intestinimonas AF211 was isolated in reinforced *clostridium* medium (RCM, available at Difco) in serial dilution rows and plating at least 3 times. The purification was confirmed by 16S rRNA gene sequencing. The strain Intestinimonas AF211 was maintained in RCM medium at 37° C.

Functional Analysis:

In order to assess the ability of Intestinimonas AF211 to convert L-lysine into butyric acid and/or butyrate and derivatives, a group of Intestinimonas AF211 was grown in a bicarbonate-buffered medium containing 20 mM L-Lysine as the sole source of carbon and energy. The ability of Intestinimonas AF211 to produce butyric acid and/or butyrate or a derivative thereof was also tested in the presence of other amino acids by growing separate groups of Intestinimonas AF211 in a bicarbonate-buffered medium containing 20 mM of D-lysine, glutamate, glutamine, glycine, proline, arginine, aspartate or methionine. Another group of Intestinimonas AF211 was grown in a bicarbonate-buffered medium containing 20 mM of glucose, galactose, arabinose, lactose, maltose, or fructose plus acetate.

Production of butyric acid and/or butyrate, as well as other products (e.g., acetate) was assessed by High Performance Liquid Chromatography (HPLC) and OD measurement by a spectrophotometer at wavelength of 600 nm. Lysine degradation was quantified on a HPLC using a Polaris C18-A column (Agilent) running at 45° C. and a UV-visible detector at wavelength of 436 nm. Flow rate was 0.5 ml/minute. A2-eluent mobile phase was consisting of 24 mM acetic acid: 8% acetonitrile (pH 6.6) as solvent A and acetonitrile:2-propanol (60:40) as solvent B. The eluent gradient was set from 95% solution A and 5% solution B to 25% of solution A and 75% of solution B was for the first 15 minutes and each run was taken for 22 minutes in total. An internal standard was 4 mM norleucine. The product formation was measured on a Thermo Scientific HPLC Spectra system equipped with a Agilent Metacarb 67H 300×6.5 mm column kept at 37° C. and running with 10 mM arabinose as an eluent. The detector was a refractive index detector. The eluent flow was 0.8 ml/minute. Gas production was performed as previously described. All analyses were performed in duplicate.

Intestinimonas AF211 was cultivated in a bicarbonate buffered medium containing 20 mM of [2-$^{13}$C] L-lysine or [6-$^{13}$C]L-lysine. Labelled lysine was purchased from Campro Scientific (Veenendaal, The Netherlands). Samples were taken from overnight growing culture and centrifuged at 10000 g. Supernatants was dissolved in 0.5 mL D20 (99.9 atom %, Sigma Aldrich) and were subsequently collected in NMR tubes (Campro scientific). $^{13}$C NMR spectra were recorded at a probe temperature of 300K on a Bruker Avance-III-500 spectrometer located at the Wageningen NMR Centre (WNMRC), Wageningen, the Netherlands. Chemical shifts were expressed in ppm relative to the C-6 of added [6-$^{13}$C] lysine at 41.75 ppm (Biological Magnetic Resonance Data Bank, the site available on the World Wide Web at bmrb.wisc.edu/metabolomics/metabolomics_standards). The products were identified based on chemical shifts as compared to above database.

Results:

The results of the experiment are shown in FIG. 1. Briefly, the results revealed that the strain Intestinimonas AF211 was able to convert L-lysine into butyrate. More specifically, it was found that Intestinimonas AF211 converted approximately 16.8 mM of L-lysine into 14.2 mM of butyrate and 15.6 mM of acetate (see FIG. 1). The results also show that no butyrate could be produced by Intestinimonas AF211 when grown in the presence of amino acids other than L-Lysine.

Example 2: Identification of the Genes Involved in the Lysine Pathway

The goal of this experiment was to determine whether Intestinimonas AF211 possesses the genes constituent of the lysine pathway. For this purpose, the genome of Intestinimonas AF211 was sequenced using single molecule next generation sequencing (NCBI accession number CP009497). The results were subsequently analyzed for the presence of genes belonging to the lysine pathway.

Genome Sequencing:

Intestinimonas AF211, which was grown in RCM (o/n), was used for DNA extraction. The DNA isolation was performed using ZR Fungal/Bacteria DNA MINIPREP™ kit (ZYMO) according to manufacturer's instructions. Genome sequencing of 15 kb library was performed with PacBio RS II instrument using P4/C2 chemistry (Pacific Biosciences, Menlo Park Calif., USA). Data processing and filtering was done with PacBio SMRT analysis pipeline v2.2 and the Hierarchical Genome Assembly Process (HGAP) protocol (World Wide Web at pacb.com/devnet).

Results:

The results show that the genome of Intestinimonas AF211 consisted of a single circular chromosome of 3,376,476 bp, which carried 3359 coding sequences that were annotated as NCBI accession number CP009497. Remarkably, the entire lysine pathway gene set (also referred to as cluster AF976-982) was found in Intestinimonas AF211. More specifically, genes that may be comprised in the lysine pathway gene set are listed in Table 1 below.

TABLE 1

Genes comprised in the lysine pathway gene set and detected in *Intestinimonas* AF211.

| | Genes comprised in the lysine pathway gene set and detected in *Intestinimonas* AF211 | Locus tag |
|---|---|---|
| 1. | L-Lysine permease | AF887 |
| 2. | Lysine 2,3-aminomutase (EC 5.4.3.2) | AF980 |
| 3. | L-beta-lysine 5,6-aminomutase alpha subunit (EC 5.4.3.3) | AF981 |
| 4. | L-beta-lysine 5,6-aminomutase beta subunit (EC 5.4.3.3) | AF982 |
| 5. | 3,5-diaminohexanoate dehydrogenase (EC 1.4.1.11) | AF979 |
| 6. | 3-keto-5-aminohexanoate cleavage enzyme | AF977 |
| 7. | 3-aminobutyryl-CoA ammonia-lyase | AF976 |
| 8. | Butyryl-CoA dehydrogenase (EC 1.3.99.2)/Etf | AF2889 to 2891 |
| 9. | Butyrate-acetoacetate CoA-transferase subunit A (EC 2.8.3.9) | AF3339 |
| 10. | Butyrate-acetoacetate CoA-transferase subunit B (EC 2.8.3.9) | AF3340 |
| 11. | Acetyl-CoA:acetoacetyl-CoAtransferase (EC 2.8.3.8) | AF155 |
| 12. | 3-ketoacyl-CoA thiolase (EC 2.3.1.16)/Acetyl-CoA acetyltransferase (EC 2.3.1.9) | AF3338 |
| 13. | Phosphate acetyltransferase (EC 2.3.1.8) | AF212 |
| 14. | Acetate kinase (EC 2.7.2.1) | AF1052 |
| 15. | Proton pumping Rnf cluster (A, B, C, D, E, G subunits) | AF682 to 687 |
| 16. | V-type ATP synthase cluster (A, B, C, D, E, F, I, K subunits) | AF3050 to 3057 |
| 17. | Inorganic Pyrophosphatase (EC 3.6.1.1) | AF2617 |
| 18. | Ammonium transporter | AF653, AF1882, AF1747, AF2982, AF3082, AF3208 |
| 19. | Putative short chain fatty acids transporter | AF191, AF924, AF1158 |
| 20. | Na+/H+ antiporter | AF1159, AF2156, AF3116 |

Example 3: Proteomic Analysis of the Lysine Utilization Pathway

In order to assess whether Intestinimonas AF211 is able to produce the proteins encoded by the genes of the lysine degradation pathway (see Table 1, Example 2), the following experiment was performed:

Culture:

A first group of Intestinimonas AF211 was grown on in 500 ml of bicarbonate buffer medium comprising 20 mM L-lysine as the sole source of carbon and energy. A second group of Intestinimonas AF211 was grown in 500 ml of bicarbonate buffer medium comprising 40 mM glucose and 40 mM of sodium acetate (GA) as the sole source of carbon and energy. In a subsequent step, the proteins produced by both groups were harvested by collecting Intestinimonas AF211 of each experimental condition in the exponential phase by centrifugation at 10000×g at 4° C. for 20 minutes. The pellets obtained were subsequently washed twice in 100 mM Tris-HCl, pH 7.5, 1 mM dithioerythreitol (DTE) and suspended in 1 ml of SDT-lysis buffer, which contained 100 mM Tris/HCl pH 7.5, 4% SDS and 0.1 M dithiotreitol. In a subsequent step the proteins were extracted according to the method of Bennett et al. (1995), *FEMS Microbiology Reviews*, Vol: 17, pages 241-249. The abundance of the proteins extracted from each of the experimental conditions was investigated with LC-MS/MS.

Protein Analysis:

A quantitative proteomics analysis was carried out a on the cytoplasmic protein fraction. For this purpose, an Intestinimonas AF211 database was deduced from its genome sequence and used together with a contaminant database, which contained sequences of common contaminants, for instance, BSA, trypsin, keratin, bovine serum albumin. The proteomics result contained peptides and proteins with a false discovery rate (FDR) of less than 1% and proteins with at least two identified peptides of which should be unique and one should be unmodified without any reversed hits. The normal logarithm was taken from protein label free quantitation (LFQ) intensities. Zero "Log LFQ" values were replaced by a value of 5.4 (just below the lowest value) to make sensible ratio calculations possible. Relative protein quantitation of sample to control was done with Perseus 1.3.0.4 by applying a two sample T-test using the "LFQ intensity" columns obtained with FDR set to 0.05 and S0 set to 1. Total non-normalized protein intensities corrected for the number of measurable tryptic peptides were giving intensity based absolute quantitation intensity (iBAQ). Total proteins were quantified using QUBIT® 2.0 Fluorometer (Invitrogen) according to manufacturer's instructions.

Results:

The results of the proteomic analysis revealed that Intestinimonas AF211 is able to produce all proteins involved in the conversion of L-lysine into butyrate and employed the lysine utilization pathway as taught herein (i.e., encoded by genes comprised in the Lysine pathway gene set AF976-982; see Table 1, Example 2). The results also show that Intestinimonas AF211 was able to produce all proteins involved in the conversion of glucose and acetate into butyrate and employed the acetyl-CoA pathway, similar to other members of *Clostridium* cluster IV. Taken together, these results indicate that Intestinimonas AF211 comprises both the lysine utilization pathway (as taught herein) and the conventional acetyl-CoA pathway.

Moreover, it was found that the production of proteins encoded by the lysine pathway genes was up-regulated when Intestinimonas AF211 was grown in the presence of L-lysine as the sole source of carbon and energy as compared to when Intestinimonas AF211 was grown in the presence of equimolar amounts of glucose and acetate (GA) as the sole source of carbon and energy. For instance, it was observed by the present inventors that the following proteins were upregulated in the presence of L-lysine relative to GA as the sole carbon source: acetyl-CoA: acetoacetyl-CoA transferase (4.08-fold increase); phosphate acetyltransferase (3.25-fold increase), 3-keto-5-aminohexanoate cleavage enzyme (10.87-fold increase); 3,5-diaminohexanoate dehydrogenase (7.07-fold increase); lysine 2,3-aminomutase (11.11-fold increase); L-beta-lysine 5,6-aminomutase alpha subunit (6.25-fold increase); L-beta-lysine 5,6-aminomutase beta subunit (11.26-fold increase); acetate kinase (2.83-fold increase); 3-ketoacyl-CoA thiolase/Acetyl-CoA acetyltransferase (1.34-fold increase); butyrate-acetoacetate CoA-transferase (1.57-fold increase); and butyrate-acetoacetate CoA-transferase beta subunit (2.03-fold increase).

Example 4: Metabolism of Amadori Glycated Products

The goal of this experiment was to assess whether Intestinimonas AF211 was capable of growing efficiently on a medium comprising fructose-lysine and whether Intestinimonas AF211 was able to convert fructose-lysine into butyrate. Further, the genome of Intestinimonas AF211 was analyzed and screened for the presence of the genes comprised in the fructose-lysine uptake and degradation operon.

Functional Analysis:

In order to assess whether Intestinimonas AF211 is able to metabolize Amadori glycated lysine (fructose-lysine), Intestinimonas AF211 was grown in a bicarbonate medium comprising 20 mM of fructose-lysine for a duration of 4 days.

Results:

The results of the genome analysis revealed that Intestinimonas AF211 possesses an operon-like cluster with genes for fructose-lysine uptake and degradation (AF949-955). The genes are listed in Table 2 below.

The results of the functional analysis reveal that Intestinimonas AF211 was not only capable of growing efficiently on a fructose-lysine substrate but was also able to convert fructose-lysine into butyrate. More specifically, it was shown that Intestinimonas AF211 was able to convert 20 mM of fructose-lysine into 16.4 mM of butyrate, 0.2 mM of acetate, and 9.4 mM of ammonium ($NH_4+$) over a period of 4 days.

TABLE 2

The Fructose-lysine uptake and degradation pathway

| | Genes comprised in the fructose-lysine uptake and degradation operon and detected in *Intestinimonas* AF211 | Locus tag |
|---|---|---|
| 1. | Fructose-lysine kinase | AF949 |
| 2. | Fructoselysine 3-epimerase | AF950 |
| 3. | Fructosamine deglycase | AF951 |
| 4. | ABC transporter periplasmic spermidine putrescine-binding protein PotD | AF952 |
| 5. | Spermidine Putrescine ABC transporter permease component PotC | AF953 |
| 6. | Spermidine putrescine ABC transporter permease component PotB | AF954 |
| 7. | Putrescine transport ATP-binding protein PotA | AF955 |

Example 5: Proteomic Analysis of the Fructose-Lysine Uptake and Degradation Pathway In order to assess whether Intestinimonas AF211 was able to produce the proteins encoded by the genes of the fructose-lysine uptake and degradation pathway (see Table 2, Example 4), the following experiment was performed:

Culture:

A first group of Intestinimonas AF211 was grown in 500 ml of bicarbonate buffer medium comprising 20 mM of lysine as the sole source of carbon and energy. A second group of Intestinimonas AF211 was grown in 500 ml of bicarbonate buffer medium comprising 40 mM glucose and 40 mM of sodium acetate (GA) as the sole source of carbon and energy. In a subsequent step, the proteins produced by both groups were harvested by collecting Intestinimonas AF211 of each experimental condition in the exponential phase by centrifugation at 10000×g at 4° C. for 20 minutes. The pellets obtained were subsequently washed twice in 100 mM Tris-HCl, pH 7.5, 1 mM dithioerythreitol (DTE) and suspended in 1 ml of SDT-lysis buffer, which contained 100 mM Tris/HCl pH 7.5, 4% SDS and 0.1 M dithiotreitol. In subsequent steps, the proteins were extracted according to the method of Bennett et al. (1995), *FEMS Microbiology Reviews*, Vol: 17, pages 241-249. The abundance of the proteins extracted from each of the experimental conditions were investigated with LC-MS/MS.

Protein Analysis:

A quantitative proteomics analysis was carried out a on the cytoplasmic protein fraction as set out in Example 3 above.

Results:

The results of the proteomic analysis revealed that Intestinimonas AF211 is also able to produce all proteins involved in the conversion of fructose-lysine into butyrate and employed the fructose-lysine uptake and degradation pathway as taught herein (see Table 2, Example 3).

Moreover, it was found that the production of proteins encoded by the fructose-lysine uptake and degradation pathway genes as taught herein were up-regulated when Intestinimonas AF211 was grown in the presence of lysine as the sole source of carbon and energy compared to when Intestinimonas AF211 was grown in the presence of GA as the sole source of carbon and energy. For instance, it was observed by the present inventors that the following proteins were upregulated in the presence of lysine relative to GA: fructose-lysine kinase (16.51-fold increase); fructosamine deglycase (9.42-fold increase); ABC transporter periplasmic spermidine putrescine-binding protein PotD (2.78-fold increase); spermidine putrescine ABC transporter permease component PotC (24.8-fold increase); and putrescine transport ATP-binding protein PotA (20.21-fold increase).

Example 6: Antibiotic Sensitivity of Intestinimonas Strain AF211

Rettedal et al. (*Nature Comm.* (2014), 5:4714) describe the use of antibiotics to isolate and culture bacteria from the human intestinal tract. However, this approach often results in antibiotic-resistant bacteria and these are undesired in formulations aimed for human or animal use. The Intestinimonas strain P1C2 that was isolated was described as resistant to erythromycin (MIC 32 ug/ml), an macrolide antibiotic often used in humans. Hence, the sensitivity of Intestinimonas strain AF211 against erythromycin was determined. It was found that strain AF211 was sensitive to erythromycin, having an MIC of 1 μg/ml erythromycin.

Strain AF211 had the following sensitivity to various antibiotics:

| Antibiotic | MIC (μg/ml) |
|---|---|
| Cefotaxime | 0.064-0.05 |
| Erythromycin | 0.75-1 |
| Oxacillin | 0.38 |
| Teicoplanin | 0.047 |
| Tobramycin | 2 |
| Vancomycin | 0.75 |

The invention claimed is:

1. A method of providing treatment of metabolic syndrome in a subject, the method comprising:
 administering to the subject a bacterium comprising:
 a lysine pathway gene set that enables said bacterium to convert L-lysine into butyric acid, butyrate, or a combination or derivative thereof, and
 a glycated lysine uptake and degradation operon that enables said bacterium to convert glycated lysine into butyric acid, butyrate, or a combination or derivative thereof,
 wherein the lysine pathway gene set encodes at least one of Lysine 2,3-aminomutase, L-beta-lysine 5,6-aminomutase alpha subunit, L-beta-lysine 5,6-aminomutase beta subunit, 3,5-diaminohexanoate dehydrogenase, 3-keto-5-aminohexanoate cleavage enzyme, 3-aminobutyryl-CoA ammonia-lyase, butyrateacetoacetate CoA-transferase subunit A, butyrate-acetoacetate CoA-transferase subunit B, and acetyl-CoA:acetoacetyl-CoA transferase; and
 wherein the glycated lysine uptake and degradation operon is a fructose-lysine uptake and degradation operon encoding at least one of fructose-lysine kinase, fructosamine deglycase, ABC transporter periplasmic spermidine putrescine-binding protein PotD, spermidine putrescine ABC transporter permease component PotC, spermidine putrescine ABC transporter permease component PotB, and putrescine transport ATP-binding protein PotA.

2. The method according to claim 1, wherein when the bacterium is grown on L-lysine as the sole carbon source as compared to when the bacterium is grown on equimolar amounts of glucose and acetate as sole carbon source,
 expression of at least one of the genes encoding the proteins: Lysine 2,3-aminomutase, L-beta-lysine 5,6-aminomutase alpha subunit, L-beta-lysine 5,6-aminomutase beta subunit, 3,5-diaminohexanoate dehydrogenase, 3-keto-5-aminohexanoate cleavage enzyme, 3-aminobutyryl-CoA ammonia-lyase, butyrate-acetoacetate CoA-transferase subunit A, butyrate-acetoacetate CoA-transferase subunit B, and acetyl-CoA:acetoacetyl-CoA transferase, is upregulated; and/or
 at least one of the proteins: Lysine 2,3-aminomutase, L-beta-lysine 5,6-aminomutase alpha subunit, L-beta-lysine 5,6-aminomutase beta subunit, 3,5-diaminohexanoate dehydrogenase, 3-keto-5-aminohexanoate cleavage enzyme, 3-aminobutyryl-CoA ammonia-lyase, butyrate-acetoacetate CoA-transferase subunit A, butyrate-acetoacetate CoA-transferase subunit B, and acetyl-CoA:acetoacetyl-CoA transferase, is overexpressed.

3. The method according to claim 1, wherein the glycated lysine is fructose-lysine, and wherein the glycated lysine uptake and degradation operon is a fructose-lysine uptake and degradation operon.

4. The method according to claim 3, wherein the fructose-lysine uptake and degradation operon comprises a gene encoding fructose-lysine 3-epimerase.

5. The method according to claim 1, wherein when the bacterium is grown on L-lysine as the sole carbon source as compared to when the bacterium is grown on equimolar amounts of glucose and acetate as sole carbon source,
 expression of at least one of the genes encoding the proteins: fructose-lysine kinase, fructoselysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, putrescine transport ATP-binding protein PotA, is upregulated; and/or at least one of the proteins: fructose-lysine kinase, fructoselysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, putrescine transport ATP-binding protein PotA, is overexpressed.

6. The method according to claim 1, wherein the bacterium is sensitive to erythromycin, having a minimum inhibitory concentration of erythromycin of less than 20 µg/ml.

7. The method according to claim 1, wherein the glycated lysine is fructose-lysine, and wherein the glycated lysine uptake and degradation operon is a fructose-lysine uptake and degradation operon.

8. The method according to claim 3, wherein the fructose-lysine uptake and degradation operon comprises one or more of the genes encoding the proteins: fructose-lysine kinase, fructose-lysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, and putrescine transport ATP-binding protein PotA.

9. The method according to claim 8, wherein when the bacterium is grown on L-lysine as the sole carbon source as compared to when the bacterium is grown on equimolar amounts of glucose and acetate as sole carbon source, expression of at least one of the genes encoding the proteins: fructose-lysine kinase, fructoselysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, putrescine transport ATP-binding protein PotA, is upregulated; and/or at least one of the proteins: fructose-lysine kinase, fructoselysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, putrescine transport ATP-binding protein PotA, is overexpressed.

10. The method according to claim 2, wherein the glycated lysine is fructose-lysine, and wherein the glycated lysine uptake and degradation operon is a fructose-lysine uptake and degradation operon.

11. The method according to claim 10, wherein the fructose-lysine uptake and degradation operon comprises one or more of the genes encoding the proteins: fructose-lysine kinase, fructose-lysine 3-epimerase, fructosamine deglycase, ABC transporter periplasmic spermidine putrescine-binding protein PotD, spermidine putrescine ABC transporter permease component PotC, spermidine putrescine ABC transporter permease component PotB, and putrescine transport ATP-binding protein PotA.

12. The method according to claim 1, wherein the fructose-lysine uptake and degradation operon further comprises the gene encoding the protein fructose-lysine 3-epimerase.

13. The method according to claim 1, wherein the bacterium colonizes the large intestine of the subject.

14. The method according to claim 1, wherein the treatment maintains, restores, and/or improves the subject's gastrointestinal health.

15. The method according to claim 1,
wherein the lysine pathway gene set encodes each of Lysine 2,3-aminomutase, L-beta-lysine 5,6-aminomutase alpha subunit, L-beta-lysine 5,6-aminomutase beta subunit, 3,5-diaminohexanoate dehydrogenase, 3-keto-5-aminohexanoate cleavage enzyme, 3-aminobutyryl-CoA ammonia-lyase, butyrateacetoacetate CoA-transferase subunit A, butyrate-acetoacetate CoA-transferase subunit B, and acetyl-CoA:acetoacetyl-CoA transferase; and
wherein the fructose-lysine uptake and degradation operon encode each of fructose-lysine kinase, fructosamine deglycase, ABC transporter periplasmic spermidine putrescine-binding protein PotD, spermidine putrescine ABC transporter permease component PotC, spermidine putrescine ABC transporter permease component PotB, and putrescine transport ATP-binding protein PotA.

16. The method according to claim 15, wherein the fructose-lysine uptake and degradation operon further encodes fructose-lysine 3-epimerase.

17. A method of treating a subject for metabolic syndrome, wherein the subject has a large intestine, the method comprising:
administering to the subject a bacterium, wherein the bacterium is Intestinimonas AF211 deposited on Jan. 5, 2015 at the Centraalbureau voor Schimmelcultures located in Utrecht, the Netherlands, and assigned deposit number CBS 139326 or a strain derived therefrom.

18. The method according to claim 17, wherein the bacterium colonizes the large intestine of the subject.

19. The method according to claim 17, wherein the treatment maintains, restores, and/or improves the subject's gastrointestinal health.

* * * * *